United States Patent
Lawandy

(10) Patent No.: US 10,082,454 B2
(45) Date of Patent: Sep. 25, 2018

(54) DEVICE AND METHOD FOR GASOCHROMIC POROSITY SENSING

(71) Applicant: Spectra Systems Corporation, Providence, RI (US)

(72) Inventor: Nabil M. Lawandy, Saunderstown, RI (US)

(73) Assignee: Spectra Systems Corporation, Providence, RI (US)

( * ) Notice: Subject to any disclaimer, the term of this patent is extended or adjusted under 35 U.S.C. 154(b) by 754 days.

(21) Appl. No.: 14/071,275

(22) Filed: Nov. 4, 2013

(65) Prior Publication Data

US 2016/0178501 A1 Jun. 23, 2016

(51) Int. Cl.
*G01N 15/08* (2006.01)
*B42D 25/29* (2014.01)
(Continued)

(52) U.S. Cl.
CPC .......... *G01N 15/088* (2013.01); *G01N 15/082* (2013.01); *G07D 7/1205* (2017.05);
(Continued)

(58) Field of Classification Search
CPC ............. G01N 1/22; G01N 2021/1795; G01N 2021/3137; G01N 2021/6419;
(Continued)

(56) References Cited

U.S. PATENT DOCUMENTS

| 5,146,086 A | * | 9/1992 | De | G01N 15/08 |
| | | | | 250/253 |
| 5,193,854 A | * | 3/1993 | Borowski, Jr. | A63F 3/0685 |
| | | | | 283/87 |
| 7,044,376 B2 | * | 5/2006 | Nelson | G06K 1/121 |
| | | | | 235/454 |

(Continued)

FOREIGN PATENT DOCUMENTS

| EP | 1918707 A2 * | 5/2008 | ............. C12Q 1/001 |
| WO | WO 2009133997 A1 * | 11/2009 | ........... G01N 21/783 |

(Continued)

OTHER PUBLICATIONS

Written Opinion of the International Searching Authority in PCT/US2014/063940 (dated May 15, 2015).
(Continued)

*Primary Examiner* — Randy Gibson
*Assistant Examiner* — Gedeon M Kidanu
(74) *Attorney, Agent, or Firm* — Pryor Cashman LLP

(57) ABSTRACT

A method and apparatus for testing the porosity of an object, such as a secure instrument having a substrate, visual data, and a security feature, is disclosed. The method and apparatus include a fluid source, a gasochromic material, an excitation source configured to excite the gasochromic material, and a detection device configured to sense changes in emissions from the gasochromic material after it is contacted with the fluid and excited by the excitation source. The object is configured to fit within a space between the fluid source and the gasochromic material such that when the fluid is emitted from the fluid source, at least a portion of the fluid is configured to flow through the object before contacting the gasochromic material.

58 Claims, 5 Drawing Sheets

(51) Int. Cl.
  *B42D 25/36* (2014.01)
  *G07D 7/14* (2006.01)
  *G07D 7/1205* (2016.01)

(52) U.S. Cl.
  CPC ............... *G07D 7/14* (2013.01); *B42D 25/29* (2014.10); *B42D 25/36* (2014.10); *G01N 2015/086* (2013.01); *G01N 2015/0846* (2013.01)

(58) Field of Classification Search
  CPC .... G01N 21/64; G01N 21/783; G01N 15/082; G01N 15/088; G01N 2015/0846; G01N 2021/6417; G01N 2021/6439; G01N 21/6408; G01N 21/643; G07D 7/122; G07D 7/14; G07D 7/1205; G07D 7/185; B42D 25/29; B42D 25/36
  See application file for complete search history.

(56) References Cited

U.S. PATENT DOCUMENTS

| | | | | |
|---|---|---|---|---|
| 7,229,593 | B1* | 6/2007 | Ho | G01N 13/00 422/50 |
| 9,075,020 | B2* | 7/2015 | Lawandy | G01N 21/783 |
| 2005/0063870 | A1* | 3/2005 | Fukushima | G01N 21/553 422/82.05 |
| 2005/0195391 | A1* | 9/2005 | Alexander | G01N 21/276 356/243.1 |
| 2006/0132786 | A1* | 6/2006 | Helbing | A61B 5/14546 356/446 |
| 2008/0110243 | A1* | 5/2008 | Burke | B01D 65/102 73/38 |
| 2009/0061076 | A1* | 3/2009 | Rosicke | G01N 21/255 427/66 |
| 2010/0090845 | A1* | 4/2010 | Polak | G01N 21/3504 340/632 |
| 2011/0199222 | A1* | 8/2011 | Lawandy | G01N 21/783 340/632 |
| 2012/0140791 | A1* | 6/2012 | Lawandy | G07D 7/12 374/45 |
| 2013/0287264 | A1* | 10/2013 | Chen | G07D 7/2016 382/112 |

FOREIGN PATENT DOCUMENTS

| | | | | |
|---|---|---|---|---|
| WO | WO 2010055308 A1 * | 5/2010 | | G01N 21/78 |
| WO | WO 2015066716 A3 * | 7/2015 | | G01N 15/082 |

OTHER PUBLICATIONS

Search Report of the International Searching Authority in PCT/US2014/063940 (dated May 15, 2015).

* cited by examiner

DEVICE AND METHOD FOR GASOCHROMIC POROSITY SENSING

TECHNICAL FIELD

The present invention relates generally to devices and methods for sensing the transmission of a gas or liquid through a material or membrane. More specifically, the present invention relates to the use of gasochromic materials to test the porosity of an object, such as a secure instrument having a substrate, visual data, and a security feature.

BACKGROUND OF THE INVENTION

High security documents such as banknotes and lottery scratch tickets have substrates formed from various materials. For example, lottery scratch tickets include security coatings configured to be removed by scratching in order to determine whether an individual has won. Moreover, in the United States, paper currency is made from a non-woven combination of 75% cotton and 25% linen fibers. In most other countries, pulp-based substrates are used. Some countries, such as Canada, have used cotton and paper blended banknotes. In addition, countries such as Australia, New Zealand and Canada have issued banknotes having polymer substrates, e.g., substrates including biaxially oriented polypropylene. The substrate, which may include one or more plies of the substrate material, may include security features such as laminated polymer or paper security threads, planchettes, and watermarks formed directly into the substrate.

As counterfeiters have become more sophisticated, the security features in such documents have had to become more advanced as well in order to prevent widespread fraud. As the substrates of such secure documents have become more advanced, the cost to produce them has also increased, thus making the replacement of worn currency quite expensive. Therefore, it is important that in addition to being secure, such documents must have a high level of durability, lack certain imperfections, and be removed from circulation when the appropriate criteria on their fitness are available.

Banknotes and lottery scratch tickets are removed from circulation for a variety of reasons. For example, lottery scratch tickets may be removed if they have pinpricks in the coating. In addition, based on one study, 81% of banknotes are removed because of soiling, 9% are removed because of damage caused by mechanical means, especially tearing, 5% are removed because of graffiti on the notes, 4% are removed because of general wear and tear, and 1% are removed because of damage to the security elements.

Banknotes have a finite time in circulation due to soling and tearing of the notes in use by the public. For example, it takes about 4,000 double folds (first forward and then backward) before a U.S. paper bill will tear. Banknotes are handled in many ways during their usable life and experience a variety of mechanical stresses, as well as being brought into contact with substances that can dirty the notes, resulting in difficulty in their authentication and use.

One important parameter used to determine the fitness of banknotes is limpness. When banknotes have been in circulation, the mechanical wear from folds, handling, and use in bill acceptors, results in a loss of mechanical elasticity that leads to the notes becoming limp. In addition, the mechanical wear of banknotes results in banknotes being torn and/or ripped. This "limpness," tearing, and ripping has been shown to be directly related to changes in the porosity of the banknote with mechanical wear. In particular, the porosity of the banknotes increases with use and manifests itself in a lower effective elastic constant.

Generally, porosity is an important physical parameter for a number of applications and as a diagnostic tool. For example, it plays a critical role in membrane separations, time released drug delivery, soil science and engineering and banknote fitness. In particular, porosity is used in a variety of fields including pharmaceuticals, ceramics, metallurgy, materials, manufacturing, earth sciences, soil mechanics, and engineering.

Typically, porosity is measured using the transport of liquids or gasses and characterizing the void fraction, physisorption, and tortuosity of the voids in a material or membrane. The detection of the gas or liquid passing through the material or membrane is measured with a variety of methods, including flow meters, mass spectrometers, absorption spectra, fluorescence, mercury intrusion, water evaporation, and mass change, computed tomography.

Specifically, with respect to banknotes, given the large numbers of banknotes in circulation for even small countries, determining the fitness of banknotes is not only of importance in cost control, but also poses a serious technical challenge in terms of processing speed and accuracy. As a result, accurate determination of the fitness of banknotes by measurement of porosity would be beneficial.

There is, therefore, a need to employ an efficient and accurate manner of identifying whether banknotes and lottery scratch tickets are torn, ripped, have been tampered with and/or have been subject to excessive mechanical wear based on the porosity of the documents in order to determine whether the documents should remain in circulation or be destroyed.

SUMMARY OF THE INVENTION

It is an object of the present invention to provide an apparatus and method for testing the porosity of a material, membrane, or other object, such as a secure instrument, including a banknote or a lottery ticket.

In general, one aspect of the invention includes an apparatus for testing the porosity of an object, which may include a fluid source, a gasochromic material, an excitation source configured to excite the gasochromic material, and a detection device configured to sense changes in emissions from the gasochromic material after it is contacted with the fluid and excited by the excitation source. The object may be configured to be disposed between the fluid source and the gasochromic material such that when the fluid is emitted from the fluid source, at least a portion of the fluid is configured to flow through the object before contacting the gasochromic material.

Implementations of the invention may include one or more of the following features. The fluid source may include a gas or liquid rich in oxygen. The fluid source may include a gas or liquid containing substantially no oxygen. The gasochromic material may include molecules configured to emit light under excitation from the excitation source. The gasochromic material may be a film or a coating disposed on a transparent substrate. The excitation source may include at least one of an LED, a laser, and a lamp. The detection device may include at least one filter and at least one of photodiodes, photomultipliers, and photovoltaic cells. The object may be a material or a membrane. The detection device may include an imaging device. The object may be a lottery scratch ticket or a secure instrument, such as a banknote, including a substrate, visual data, and a security feature. The apparatus may include a device for maintaining the object in a space between the fluid source and the gasochromic material. The lottery scratch ticket may include a scratch layer and a printed data layer. The gasochromic material may be located between the scratch layer and the printed data layer. Light from the excitation source may be configured to penetrate the scratch layer. The emissions from the gasochromic material may be configured to penetrate the scratch layer. The apparatus may include a transport device for advancing the object through the space between the fluid source and the gasochromic material. The fluid source may include a valve or a line gas source. The apparatus may further comprise a transparent substrate doped with gasochromic moieties as the gasochromic material.

In general, another aspect of the invention includes a method for testing the porosity of an object. The method may include positioning the object between a fluid source and a gasochromic material, dispensing a fluid from the fluid source toward the object such that at least a portion of the fluid flows through the object and contacts the gasochromic material, exciting the gasochromic material with an excitation source, and determining the porosity of the material or membrane based on sensed changes in emissions from the gasochromic material obtained from a detection device after the gasochromic material is contacted with fluid from the fluid source and excited by the excitation source.

Implementations of the invention may include one or more of the following features. Dispensing a fluid from the fluid source may include dispensing a gas or liquid rich in oxygen. Dispensing a fluid from the fluid source may include dispensing a gas or liquid containing substantially no oxygen. Exciting the gasochromic material with an excitation source may include exciting the gasochromic material with at least one of an LED, a laser, or a lamp. Determining the porosity may include sensing changes in emissions the gasochromic material using at least one filter and at least one of photodiodes, photomultipliers, or photovoltaic cells. Positioning the object may include securing the object between the fluid source and the gasochromic material. Dispensing fluid from the fluid source may include dispensing fluid through a valve. Dispensing fluid from the fluid source may include dispensing fluid through a line gas source. The method may further include advancing the object through a space between the fluid source and the gasochromic material, such that when the object is advanced through the space, the fluid source dispenses fluid along a length of the object and the detection device obtains a plurality of images along the length of the object. The object may be a material or a membrane. The object may be a lottery scratch ticket or a secure instrument, such as a banknote, including a substrate, visual data, and a security feature. Determining the porosity may include calculating an average porosity along the length of the object. The lottery scratch ticket may include a scratch layer and a printed data layer. The gasochromic material may be located between the scratch layer and the printed data layer. Light from the excitation source may penetrate the scratch layer. The emissions from the gasochromic material may penetrate the scratch layer.

In general, another aspect of the invention may include an apparatus for testing the porosity of a secure instrument including a substrate, visual data, and a security feature. The apparatus may include a fluid source, a gasochromic material, an excitation source configured to excite gasochromic molecules in the gasochromic material, and a detection device configured to sense changes in emissions from the gasochromic material after the gasochromic material is contacted with fluid from the fluid source and excited by the excitation source. The secure instrument may be configured to be disposed within a space between the fluid source and the gasochromic material such that when the fluid source dispenses fluid, at least a portion of the fluid flows through the secure instrument before contacting the gasochromic material.

Implementations of the invention may include one or more of the following features. The secure instrument may be a banknote. The detection device may be configured to detect open and closed tears in the banknote. The fluid source may include a valve or a line gas source. The excitation source may include an LED, a laser, or a lamp. The detection device may include at least one filter and at least one of photodiodes, a photomultipliers, or photovoltaic cells. The detection device may include an imaging device. The gasochromic material may be a coating or film mounted on a transparent substrate. The apparatus may further comprise a transparent substrate doped with gasochromic moieties as the gasochromic material.

In general, another aspect of the invention may include a method for testing the porosity of a secure instrument including a substrate, visual data, and a security feature. The method may include positioning the secure instrument between a fluid source and a gasochromic material mounted on a substrate, dispensing a fluid from the fluid source in the direction of the secure instrument such that at least a portion of the fluid flows through the material or membrane and contacts the gasochromic material, exciting the gasochromic material with an excitation source, and determining the porosity of the secure instrument based on sensed changes emissions in the excited gasochromic material from a detection device.

Implementations of the invention may include one or more of the following features. Dispensing the fluid from the fluid source may include dispensing a gas or liquid rich in oxygen. Dispensing the fluid from the fluid source may include dispensing a gas or liquid containing substantially no oxygen. Exciting the gasochromic material with the excitation source may include directing light from an LED, a laser, or a lamp on the gasochromic material. Determining the porosity of the secure instrument may include using at least one filter and at least one of photodiodes, photomultipliers, and photovoltaic cells to sense the changes in emissions from the excited gasochromic material. Determining the porosity of the secure instrument may include detecting open or closed tears in the secure instrument. The method may further include advancing the secure instrument through a space between the fluid source and the gasochromic material, such that the fluid source dispenses fluid along a length of the secure instrument as the secure instrument is advanced through the space, and such that the detection device senses changes in emissions from the gasochromic material as the secure instrument is advanced through the space. The gasochromic material may be a coating or film, and the substrate may be transparent.

BRIEF DESCRIPTION OF THE DRAWINGS

The above-mentioned and other aspects, features and advantages can be more readily understood from the following detailed description with reference to the accompanying drawings, wherein.

DETAILED DESCRIPTION OF THE PREFERRED EMBODIMENTS

The present invention provides for apparatus and methods for sensing the transmission of a gas or liquid through an object, material, or membrane. More specifically, the present invention provides for methods and apparatus for measuring the porosity of secure instruments, such as banknotes and lottery scratch tickets in order to determine whether the secure instruments are ripped, have a tear, have been tampered with, or have been exposed to a high amount of mechanical wear. It should be noted, however, that the present invention should not be limited to use with secure instruments. The present invention may be used to measure the porosity of any desired object, material, or membrane.

Figure 1:
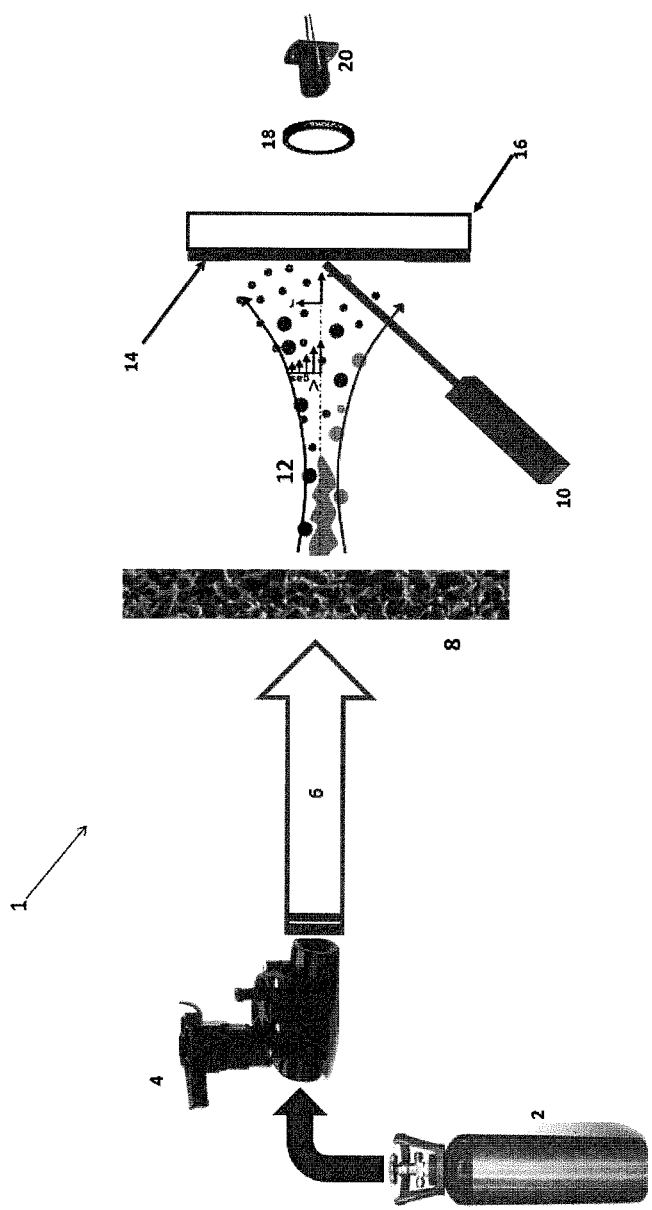
FIG. 1 is a diagram of an apparatus for testing the porosity of an object, such as a banknote, according to an embodiment of the present disclosure.

FIG. 1 illustrates a diagram of an apparatus 1 for testing the porosity of a secure instrument 8, according to an embodiment of the present disclosure. The apparatus 1 may include a fluid container 2, a fluid dispenser or source 4. The fluid source 4 may be any device known to those skilled in the art that is configured to dispense, direct, and/or control the flow of a fluid (i.e., a liquid or a gas) including, but not limited to, a pump and a line gas source. In the embodiment of FIG. 1, for example, the fluid source 4 may be a valve. The fluid source 4 may be powered by any means known to those skilled in the art, including but not limited to, electric, hydraulic, motor, pneumatic, and manual. In addition, the fluid source 4 may include multiple fluid dispensing outlets. Alternatively, as illustrated in FIG. 1, the fluid source 4 may include a single dispensing outlet 6.

The fluid source 4 may be connected to a fluid container 2. The fluid container 2 may hold any fluid (i.e., liquid or gas) known to those skilled in the art that is capable of displacing an equilibrium concentration of oxygen in a gasochromic material 14 upon contact with the gasochromic material 14. For example, the fluid may be any liquid or gas that is rich in oxygen. Alternatively, the fluid may be any liquid or gas that contains substantially no oxygen, including, but not limited to argon, helium, xenon, and nitrogen.

As previously discussed, the fluid may be capable of displacing the equilibrium concentration of oxygen in the gasochromic material 14. The gasochromic material 14 may be any material configured to change the intensity or spectral position of its emission or absorption bands in response to various molecular moieties. For example, the gasochromic material 14 may be any desired low molecular weight polymer material known to those skilled in the art that contains gasochromic molecules. The gasochromic molecules may be any molecules configured to emit light under excitation by UV light or other wavelengths including, but not limited to, platinum, rhodium, Pt-porphyrines, and iridium containing phosphyrines and nano-crystaline zinc-oxide. For example, in one embodiment, the gasochromic material 14 may be a low molecular weight polymer coating, such as polystyrene (PS), containing gasochromic molecules. Alternatively, as illustrated in FIG. 1, the gasochromic material 14 may be a film, such as polystyrene, containing gasochromic molecules.

FIG. 1 further illustrates that the gasochromic material 14 may be mounted on a substrate 16. The substrate 16 may be any substrate configured to maintain the gasochromic material 14 in a desired position and configured to enable a detection device 20 to sense light emitted from the gasochromic material 14 when the fluid contacts the gasochromic material 14. In one embodiment, as illustrated in FIG. 1, the substrate 16 may be a transparent substrate. In alternative embodiments, the substrate 16 may be doped with gasochromic moieties.

As previously discussed, the gasochromic material 14 may be configured to emit light under excitation. FIG. 1 illustrates that excitation of the gasochromic material 14 may be accomplished via an excitation source 10. The excitation source 10 may be any device configured to emit light that is capable of causing the gasochromic molecules in the gasochromic material 14 to emit a phosphorescent transition from a triplet state to a singlet ground state. For example, the excitation source 10 may be an LED or a lamp. Alternatively, as illustrated in FIG. 1, the excitation source may be a laser.

When the gasochromic molecules in the gasochromic material 14 are in an excited state, the light emitted may be sensed by a detection device 20, which is part of the apparatus 1. The detection device 20 may be any device known to those skilled in the art that may be configured to sense light, capture images, and/or create images. In one embodiment, for example, the detection device 20 may include an imaging device, such as a camera. In addition, or alternatively, the detection device 20 may include at least one sensor (not shown) configured to sense the emitted light. The sensors may be any sensors known to those skilled in the art including, but not limited to, photodiodes, photomultipliers, and photovoltaic cells.

FIG. 1 further illustrates that the detection device 20 may include one or more filters 18. The filter 18 may be any device known to those skilled in the art configured to reject all light other than the light emitted from the gasochromic molecules. For example, in one embodiment, the filter may be a Schott red glass 610 (RG 610).

Figure 2:
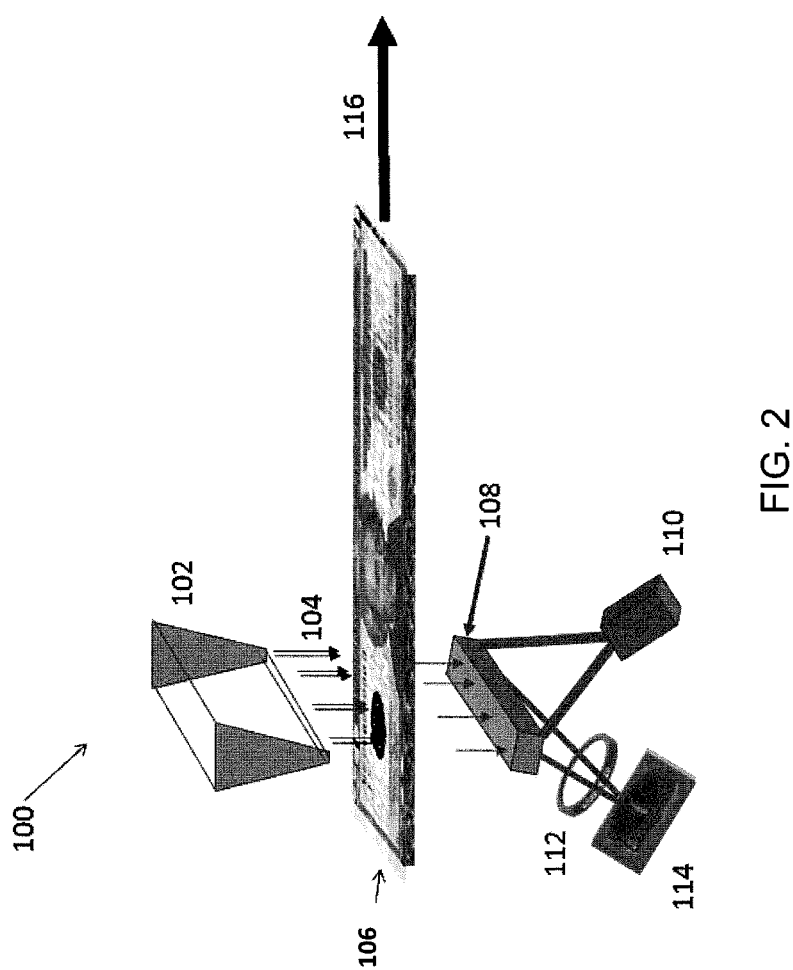
FIG. 2 is diagram of an apparatus for testing the porosity of an object according to an embodiment of the present disclosure.

FIG. 2 illustrates a diagram of an apparatus 100 for testing the porosity of a secure instrument 106 according to another embodiment of the present disclosure. The apparatus 100 of FIG. 2 may include features that are similar to the apparatus of FIG. 1. For example, the apparatus may include a fluid dispenser or source 102 configured to dispense a fluid (i.e., a liquid or a gas). The fluid source 102 may be any fluid source known to those skilled in the art that is configured to direct a flow of the fluid along a width of the secure instrument 106 as the secure instrument is advanced along its longitudinal axis 116. For example, as illustrated in FIG. 2, the fluid source 102 may be a line gas source. The fluid source 102 may further include any desired number of dispensing outlets 104 known to those skilled in the art. For example, as illustrated in FIG. 2, the fluid source 102 may contain a single dispensing outlet 104 extending along the length of the fluid source 102, and configured to extend along the width of the secure instrument 106.

Similar to FIG. 1, the fluid may be any liquid or gas configured to displace the equilibrium concentration of oxygen in a gasochromic material 108, such as a liquid or gas rich in oxygen or a liquid or gas containing substantially no oxygen. In the embodiment of FIG. 2, for example, the fluid may be a gas capable of being dispensed through the line gas source.

The apparatus 100 of FIG. 2 may further include a gasochromic material 108 mounted on a substrate that may be configured to enable a detection device 114 to sense light emitted from the gasochromic material 108 disposed on a transparent substrate. Like the gasochromic material 14 of FIG. 1, the gasochromic material of FIG. 2 may include a plurality of gasochromic molecules capable of emitting light upon receipt of light from an excitation source 110. The gasochromic material 108 may be any low molecular weight material, such as a film, that includes gasochromic molecules. Alternatively, the embodiment of FIG. 2 illustrates that the gasochromic material 108 may be a coating or may be a transparent substrate doped with gasochromic moieties.

The excitation source 110 of FIG. 2 may also be similar to the excitation source 10 of FIG. 1. For example, the excitation source 110 may be an LED, a lamp, or, as illustrated in FIG. 2, a laser. The excitation source 110 may further be configured to direct light along a single path. Alternatively, the excitation source 110 may be configured to emit light along any desired number of optical pathways known to those skilled in the art. For example, as illustrated in FIG. 2, the excitation source 110 may be configured to emit light along at least two pathways.

The apparatus 100 of FIG. 2 further includes a detection device 114. Like the detection device 20 of FIG. 1, the detection device 114 of FIG. 2 may include at least one filter 112 configured to reject all light other than the light emitted from the gasochromic molecules in the gasochromic material 108. In addition, the detection device 114 may include any device known to those skilled in the art that may be configured to sense light, capture images, and/or create images. The detection device 114 may also include at least one sensor (not shown) configured to sense the emitted light. The sensors may be any sensors known to those skilled in the art including, but not limited to, photodiodes, photomultipliers, and photovoltaic cells. For example, in the embodiment of FIG. 2, the detection device 114 may be a line scan camera. In addition, as illustrated in FIG. 2, the detection device 114 may be configured to obtain a plurality of images of the light emitted from the gasochromic molecules as the secure instrument 106 is advanced through a space between the fluid source 102 and the gasochromic material 108 along the longitudinal axis 116 of the secure instrument 106.

Figure 4B:
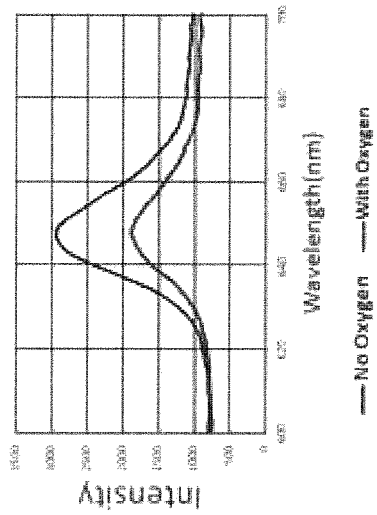
FIGS. 4A and 4B are graphs comparing the emission of gasochromic molecules in response to contact with a fluid rich in oxygen and a fluid containing substantially no oxygen.
Figure 4A:
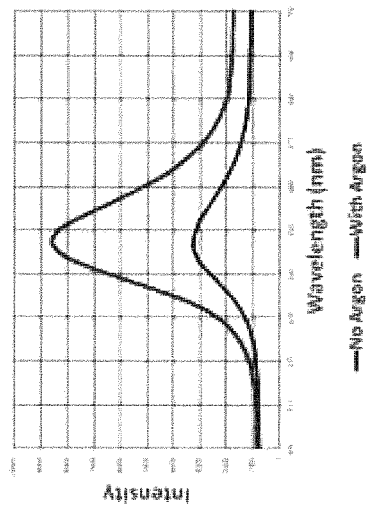

The apparatus 1 of FIG. 1 and the apparatus 100 of FIG. 2 may also each include a processor (not show) known to those skilled in the art. The processor may be configured to receive the detected images from the detection devices and output porosity data based on the detected images. The porosity data may include data corresponding to the light emitted from the gasochromic molecules in the gasochromic material 14, 108. For example, as illustrated in FIG. 4A, when a fluid that is rich in oxygen is dispensed to flow through the secure instrument 8, 106, the light that is emitted from the gasochromic material is inversely related to the porosity of the material: a lower detection of emitted light corresponds to a higher level of porosity. Conversely, as illustrated in FIG. 4B, when a fluid that has substantially no oxygen is dispensed to flow through the secure instrument 8, 106, the detected emitted light is directly related to the porosity of the material: a lower detection of emitted light corresponds to a lower level of porosity.

Figure 5B:
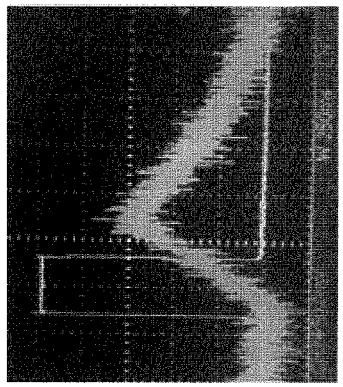
FIGS. 5A and 5B are graphs comparing the porosity of an uncirculated banknote and a circulated banknote.
Figure 5A:
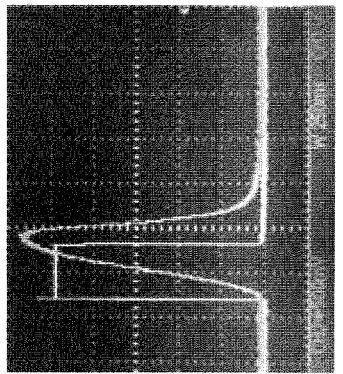

FIGS. 5A and 5B illustrate porosity data of a circulated banknote (FIG. 5A) and an uncirculated banknote (FIG. 5B) that have been tested using the apparatus of FIG. 1 with fluid containing substantially no oxygen. Typically, uncirculated banknotes have a lower porosity than circulated banknotes, because the uncirculated banknotes have not been exposed to mechanical wear. The porosity data shown in FIGS. 5A and 5B is consistent with this fact. As illustrated in FIGS. 5A and 5B, the porosity test of the circulated banknote (FIG. 5A) detected more emitted light from the gasochromic material than the porosity test of the uncirculated banknote (FIG. 5B).

Referring back to FIGS. 1 and 2, the present disclosure includes a method of testing the porosity of an object, material, or membrane. The method may first include positioning a positioning the object, material, or membrane in a space between the fluid source 4, 102 and the gasochromic material 14, 108. In the embodiment of FIG. 1, the object, material, or membrane may be positioned such that it may be secured between the fluid source 4 and the gasochromic material 14. For example, apparatus 1 may include a device configured to maintain the material or membrane in a substantially flat position, such as a plate (not shown). The device (i.e., plate) may also be configured to attach to the fluid source 4 and enable the fluid source 4 to dispense the fluid through the material or membrane. Alternatively, as illustrated in FIG. 2, the object, material, or membrane may be positioned such that the object, material, or membrane may be advanced along its longitudinal axis 116, and thereby movable relative to the fluid source 102, the gasochromic material 108, and the detection device 114.

As previously discussed, the object, material, or membrane may be any sample where porosity testing is desired. Samples may be used from a variety of fields including, but not limited to, pharmaceuticals, ceramics, metallurgy, materials, manufacturing, earth sciences, soils mechanics, and engineering. The embodiments of FIGS. 1 and 2 illustrate that the object, material, or membrane sample may in the form of a secure instrument 8, 106. The secure instrument 8, 106 may be a banknote having a substrate, visual data, and a security feature. The banknote may be any banknote from any country, including but not limited to, banknotes from the United States, China, Europe, Russia, Canada and India.

Figure 3:
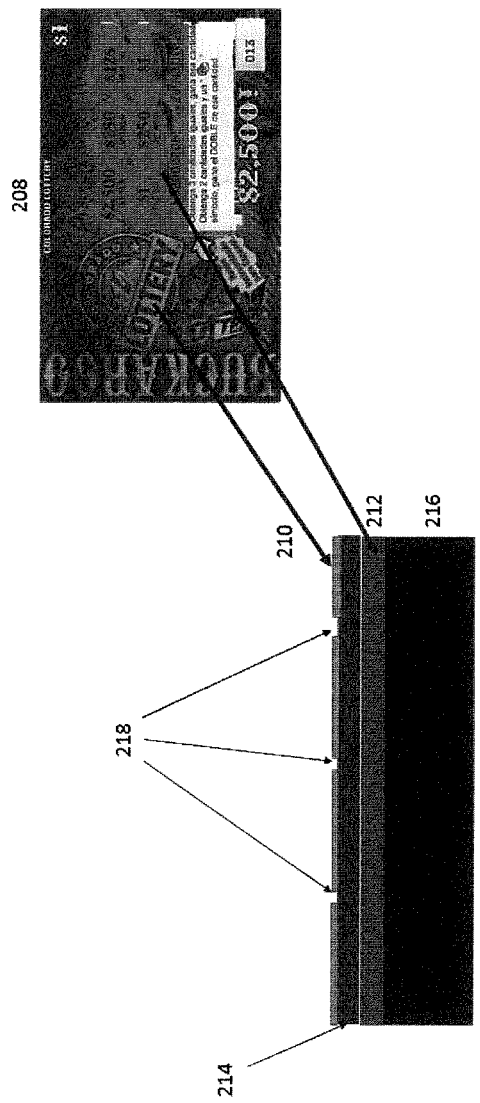
FIG. 3 is a diagram of a lottery scratch ticket according to an embodiment of the present disclosure.

FIGS. 1 and 2 illustrate a sample where it is desired to obtain characteristics about the porosity of the entire sample. Alternatively, as illustrated in FIG. 3, the object, material, or membrane may be a sample including multiple layers, such that porosity of one of the layers may be obtained. For example, FIG. 3 illustrates that the object may be a lottery scratch ticket 208 that includes a scratch layer 210 and printed data layer 212. The printed data 212 may be covered by the scratch layer 210. Because lottery scratch tickets are subject to tampering, it may be desirable to obtain characteristics about the porosity of the scratch layer 210. For example, it may be necessary to determine whether there are pinpricks 218 in the scratch layer 210 that provide access to the printed data 212.

In order to obtain porosity data corresponding to the scratch layer 210, FIG. 3 illustrates that a layer of gasochromic material 214 may be located on the lottery scratch ticket 208 between the scratch layer 210 and the printed data 212. Like the embodiments of FIGS. 1 and 2, the gasochromic material 214 may be any low molecular weight material, such as a film or coating that includes gasochromic molecules. The gasochromic material 214 may further be a transparent material such that the printed data 212 may be visually accessed upon removal of the scratch layer 210. Alternatively, or in addition, the gasochromic material 214 may be configured to be removed with the scratch layer 210 when the scratch layer 210 is subject to scratching, scraping, or the like.

FIG. 3 further illustrates that the lottery scratch ticket 208 may be mounted on a substrate 216. Like the embodiments of FIGS. 1 and 2, the substrate 216 may be a transparent substrate. To determine the porosity of the scratch layer 210, the embodiment of FIG. 3 may be used in conjunction with the fluid sources 4, 102, excitation sources 10, 110, filters 18, 112, and detection devices 20, 114 of FIGS. 1 and 2. The scratch layer 210 may be any material known to those skilled in the art and configured to be removed upon scratching, scraping, or the like. In addition, the scratch layer 210 may be any material configured to allow penetration of light from the excitation sources 10, 110 and emissions from the excited gasochromic molecules in the gasochromic material 214.

Returning to FIGS. 1 and 2, after the object, material, or membrane is positioned in the space between the fluid source 4, 102 and the gasochromic material 14, 108, fluid may be dispensed through the outlets 6, 104 of the fluid source 4, 102 such that at least a portion of the dispensed fluid 12 can flow through the object, material, or membrane. As illustrated in FIGS. 1 and 2, fluid that flows completely through the object, material, or membrane may contact the gasochromic material 14, 108 and may quench light emission of the gasochromic molecules in the gasochromic material 14, 108. In particular, FIG. 1 illustrates that the portion of the dispensed fluid 12 that flows from a side of the secure instrument 8 facing the fluid source 4 to a side of the secure instrument 8 facing the gasochromic material 14 may disperse along a width of the gasochromic material 14. For example, as illustrated in FIG. 1, at least some of the portion of the dispensed fluid 12 may disperse in a direction substantially perpendicular to a flow path of the fluid through the secure instrument 8.

The method further includes powering the excitation source 10, 110, such that the excitation source 10, 110 may emit UV or other wavelengths configured to excite the gasochromic molecules in the gasochromic material 14, 108. The excitation source 10, 110 may be positioned such that at least one path of light from the excitation source intersects with the gasochromic material 14, 108. In addition, the excitation source 10, 110 may be powered prior to, during, and after the fluid contacts the gasochromic material 14, 108, so that the detection device may be capable of detecting emitted light corresponding to the equilibrium concentration of oxygen in the gasochromic material 14, 108, and emitted light corresponding to the displaced equilibrium concentration of oxygen in the gasochromic material 14, 108. Thus, the porosity of the object, material, or membrane is related to the change in the detected emitted light corresponding to the equilibrium concentration of oxygen in the gasochromic material 14, 108 and the detected emitted light corresponding to the displaced equilibrium concentration of oxygen in the gasochromic material 14, 108.

During excitation of the gasochromic molecules in the gasochromic material 14, 108, the detection device 20, 114 may be detecting the emitted light by first, using the filter 18, 112 to reject all light other than the light emitted from the gasochromic molecules. After filtering the light, the detection device 20, 114 may use the sensors therein to detect the emitted light. The detection device 20, 114 may further transmit the detected light signals to the processor (not shown), which may be configured to determine and output data corresponding to the porosity and thereby the fitness (e.g., mechanical wear, rips, pinpricks, and tears) of the object, material, or membrane used in conjunction with the apparatus 1, 100 by analyzing the information received from the detection device 20, 114.

The determination and output of data corresponding to the porosity of the object, material or membrane may be calculated based on an average porosity over the entire material or membrane. For example, in the embodiment of FIG. 1, the secure instrument 8 may be secured between the fluid source 4 and the gasochromic material 14; and the fluid source 4 may be configured to dispense the fluid on the secure instrument 8 such that a porosity determination may be made across the entire note.

Alternatively, porosity may be determined along the length of the banknote 106. As illustrated in FIG. 2, the secure instrument 106 may be positioned in a space between the fluid source 102 and the gasochromic material 108. The secure instrument 106 may be advanced through the space along its longitudinal axis 116. As the secure instrument 106 is advanced through the space, the fluid source 102 may dispense fluid along the length of the secure instrument 106, such that the detection device 114 may obtain data corresponding to the porosity of the secure instrument 106 along its length.

The embodiments and examples above are illustrative, and many variations can be introduced to them without departing from the spirit of the disclosure or from the scope of the appended claims. For example, elements and/or features of different illustrative and exemplary embodiments herein may be combined with each other and/or substituted with each other within the scope of this disclosure. The objects of the invention, along with various features of novelty which characterize the invention, are pointed out with particularity in the claims annexed hereto and forming a part of this disclosure. For a better understanding of the invention, its operating advantages and the specific objects attained by its uses, reference should be had to the accompanying drawings and descriptive matter in which there is illustrated a preferred embodiment of the invention.

What is claimed is:

1. An apparatus for testing a porosity of an object, comprising:
   a fluid source;
   a gasochromic material;
   an excitation source configured to excite the gasochromic material; and
   a detection device configured to sense changes in emissions from the gasochromic material after it is contacted with the fluid and excited by the excitation source;
   wherein the object is configured to be disposed between the fluid source and the gasochromic material such that when the fluid is emitted from the fluid source at least a portion of the fluid is configured to flow through the object before contacting the gasochromic material.

2. The apparatus of claim 1, wherein the fluid source includes a gas or liquid rich in oxygen.

3. The apparatus of claim 1, wherein the fluid source includes a gas or liquid containing substantially no oxygen.

4. The apparatus of claim 1, wherein the gasochromic material includes molecules configured to emit light under excitation from the excitation source.

5. The apparatus of claim 1, wherein the gasochromic material is a film or a coating disposed on a transparent substrate.

6. The apparatus of claim 1, further comprising a transparent substrate doped with gasochromic moeties for the gasochromic material.

7. The apparatus of claim 1, wherein the excitation source includes at least one of an LED, a laser, and a lamp.

8. The apparatus of claim 1, wherein the detection device includes at least one filter and at least one of photodiodes, photomultipliers, and photovoltaic cells.

9. The apparatus of claim 1, wherein the detection device includes an imaging device.

10. The apparatus of claim 1, wherein the object is a material or a membrane.

11. The apparatus of claim 1, further comprising a device for maintaining the object between the fluid source and the gasochromic material.

12. The apparatus of claim 1, further comprising a transport device for advancing the object through the space between the fluid source and the gasochromic material.

13. The apparatus of claim 1, wherein the fluid source includes a valve.

14. The apparatus of claim 1, wherein the fluid source includes a line gas source.

15. The apparatus of claim 1, wherein the object is a secure instrument including a substrate, visual data, and a security feature.

16. The apparatus of claim 15, wherein the secure instrument is a banknote.

17. The apparatus of claim 1, wherein the object is a lottery scratch ticket comprising a scratch layer and a printed data layer.

18. The apparatus of claim 17, wherein the lottery scratch ticket comprising a scratch layer and a printed data layer is located between the fluid source and the gasochromic material.

19. The apparatus of claim 18, wherein light from the excitation source is configured to penetrate the scratch layer.

20. The apparatus of claim 18, wherein the emissions from the gasochromic material are configured to penetrate the scratch layer.

21. A method for testing a porosity of an object, comprising:
positioning the object between a fluid source and a gasochromic material;
dispensing a fluid from the fluid source towards the object such that at least a portion of the fluid flows through the object and contacts the gasochromic material;
exciting the gasochromic material with an excitation source; and
determining the porosity of the object based on sensed changes in emissions from the gasochromic material obtained from a detection device after the gasochromic material is contacted with fluid from the fluid source and excited by the excitation source.

22. The method of claim 21, wherein dispensing a fluid from the fluid source includes dispensing a gas or liquid rich in oxygen.

23. The method of claim 21 wherein dispensing a fluid from the fluid source includes dispensing a gas or liquid containing substantially no oxygen.

24. The method of claim 21, wherein exciting the gasochromic material with the excitation source includes exciting the gasochromic material with at least one of an LED, a laser, or a lamp.

25. The method of claim 21, wherein determining the porosity includes sensing changes in emissions from the gasochromic material using at least one filter and at least one of photodiodes, photomultipliers, or photovoltaic cells.

26. The method of claim 21, wherein positioning the object includes securing the material or membrane between the fluid source and the gasochromic material.

27. The method of claim 21, wherein dispensing fluid from the fluid source includes dispensing fluid through a valve.

28. The method of claim 21, wherein dispensing fluid from the fluid source includes dispensing fluid through a line gas source.

29. The method of claim 21, wherein the object is a material or a membrane.

30. The method of claim 21, wherein the object is a secure instrument including a substrate, visual data, and a security feature.

31. The method of claim 30, wherein the secure instrument is a banknote.

32. The method of claim 21, further comprising advancing the object through a space between the fluid source and the gasochromic material.

33. The method of claim 32, wherein when the object is advanced through the space, the fluid source dispenses fluid along a length of the object and the detection device obtains a plurality of images along the length of the object.

34. The method of claim 33, wherein determining the porosity includes calculating an average porosity along the length of the object.

35. The method of claim 21, wherein the object is a lottery scratch ticket comprising a scratch layer and a printed data layer.

36. The method of claim 35, wherein the lottery scratch ticket comprising a scratch layer and a printed data layer is located between the fluid source and the gasochromic material.

37. The method of claim 36, wherein light from the excitation source penetrates the scratch layer.

38. The method of claim 36, wherein the emissions from the gasochromic material penetrate the scratch layer.

39. An apparatus for testing a porosity of a secure instrument including a substrate, visual data, and a security feature, comprising:
a fluid source;
a gasochromic material;
an excitation source configured to excite gasochromic molecules in the gasochromic material; and
a detection device configured to sense changes in emissions from the gasochromic material after the gasochromic material is contacted with fluid from the fluid source and excited by the excitation source;
wherein the secure instrument is configured to be disposed within a space between the fluid source and the gasochromic material such that when the fluid source dispenses fluid, at least a portion of the fluid flows through the secure instrument before contacting the gasochromic material.

40. The apparatus of claim 39, wherein the fluid source incudes a valve.

41. The apparatus of claim 39 wherein the fluid source includes a line gas source.

42. The apparatus of claim 39, wherein the excitation source includes an LED, a laser, or a lamp.

43. The apparatus of claim 39, wherein the detection device includes at least one filter and at least one of photodiodes, a photomultipliers, or photovoltaic cells.

44. The apparatus of claim 39, wherein the detection device includes an imaging device.

45. The apparatus of claim 39, wherein the gasochromic material is a coating or film mounted on a transparent substrate.

46. The apparatus of claim 39, further comprising a transparent substrate doped with gasochromic moeties for the gasochromic material.

47. The apparatus of claim 39, wherein the secure instrument is a banknote.

48. The apparatus of claim 47, wherein the detection device is configured to detect open and closed tears in the banknote.

49. A method for testing a porosity of a secure instrument including a substrate, visual data, and a security feature, comprising:
- positioning the secure instrument between a fluid source and a gasochromic material mounted on a substrate;
- dispensing a fluid from the fluid source in the direction of the secure instrument such that at least a portion of the fluid flows through the substrate and contacts the gasochromic material;
- exciting the gasochromic material with an excitation source; and
- determining the porosity of the secure instrument based on sensed changes in emissions from the excited gasochromic material obtained from a detection device.

50. The method of claim 49, wherein dispensing the fluid from the fluid source includes dispensing a gas or liquid rich in oxygen.

51. The method of claim 49, wherein dispensing the fluid from the fluid source includes dispensing a gas or liquid containing substantially no oxygen.

52. The method of claim 49, wherein exciting the gasochromic material with the excitation source includes directing light from an LED, a laser, or a lamp on the gasochromic material.

53. The method of claim 49, wherein determining the porosity of the secure instrument includes using at least one filter and at least one of photodiodes, photomultipliers, and photovoltaic cells to sense the changes in emissions from the excited gasochromic material.

54. The method of claim 49, wherein determining the porosity of the secure instrument includes detecting open or closed tears in the secure instrument.

55. The method of claim 49, wherein the gasochromic material is a coating or film, and the substrate is transparent.

56. The method of claim 49, further comprising advancing the secure instrument through a space between the fluid source and the gasochromic material.

57. The method of claim 56, wherein the fluid source dispenses fluid along a length of the secure instrument as the secure instrument is advanced through the space.

58. The method of claim 57, wherein the detection device senses changes in emissions from the gasochromic material as the secure instrument is advanced through the space.

* * * * *